United States Patent [19]
Sewell, Jr.

[11] Patent Number: 5,379,759
[45] Date of Patent: Jan. 10, 1995

[54] RETRACTOR FOR ENDOSCOPIC SURGERY

[76] Inventor: Frank K. Sewell, Jr., 1413 N. Elm, Henderson, Ky. 42420

[21] Appl. No.: 95,818

[22] Filed: Jul. 21, 1993

Related U.S. Application Data

[63] Continuation of Ser. No. 997,655, Dec. 28, 1992, abandoned, which is a continuation of Ser. No. 650,049, Feb. 4, 1991, abandoned.

[51] Int. Cl.$^6$ ............................................. A61C 3/00
[52] U.S. Cl. ....................................... 128/20; 606/192
[58] Field of Search .................. 128/20, 125; 606/192

[56] References Cited

U.S. PATENT DOCUMENTS

| | | | |
|---|---|---|---|
| 2,701,559 | 2/1955 | Cooper | 606/192 |
| 3,863,639 | 2/1975 | Kleaveland | 128/20 |
| 4,207,872 | 6/1980 | Meiri et al. | 128/4 |
| 4,219,026 | 8/1980 | Layton | 128/325 |
| 4,312,353 | 1/1982 | Schahbubian | 128/20 |
| 4,517,979 | 5/1985 | Pecenka | 128/325 |
| 4,638,803 | 1/1987 | Rand | 606/192 |
| 4,714,074 | 12/1987 | Rey et al. | 128/20 |
| 4,723,547 | 2/1988 | Kullas et al. | 128/329 R |
| 4,800,901 | 1/1989 | Rosenberg | 128/899 |
| 4,889,107 | 12/1989 | Kaufman | 128/20 |
| 4,899,747 | 2/1990 | Garren et al. | 606/192 |
| 4,990,139 | 2/1991 | Jang | 604/101 |
| 5,002,556 | 3/1991 | Ishida et al. | 606/191 |
| 5,041,092 | 8/1991 | Barwick | 604/104 |
| 5,064,434 | 11/1991 | Haber | 128/DIG. 25 |
| 5,116,305 | 5/1992 | Milder et al. | 600/18 |

Primary Examiner—Cary E. O'Connor
Attorney, Agent, or Firm—Ice Miller Donadio & Ryan

[57] ABSTRACT

A surgical retractor for endoscopic surgery is provided which includes an elastic skin enclosing a variable volume cavity which is movable through a narrow tube into a body cavity when it is deflated and may be inflated within the body cavity. The elastic skin has projections for fastening the skin to body tissues and other similar retractors. A method and system using such retractors is also provided.

12 Claims, 2 Drawing Sheets

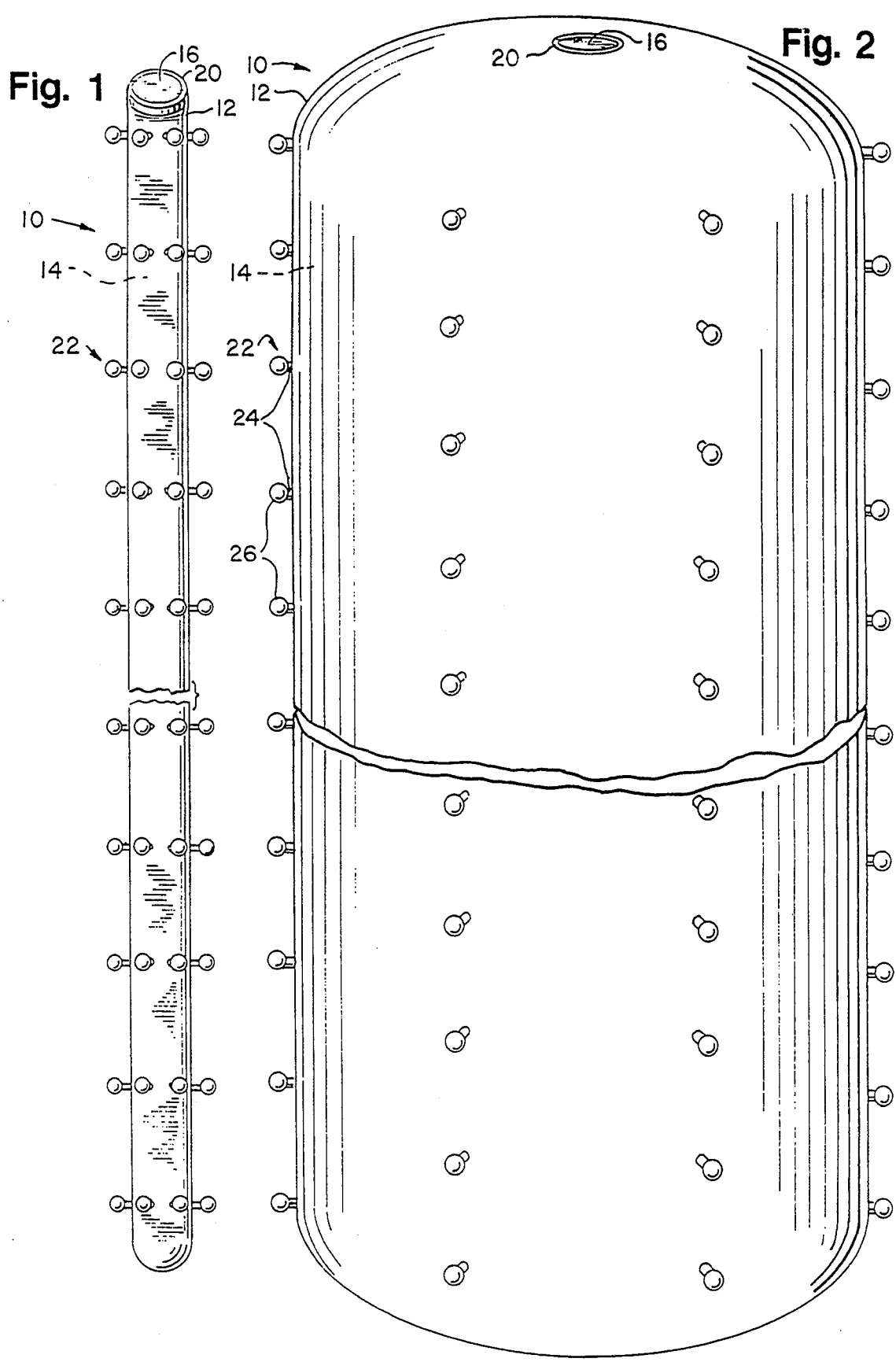

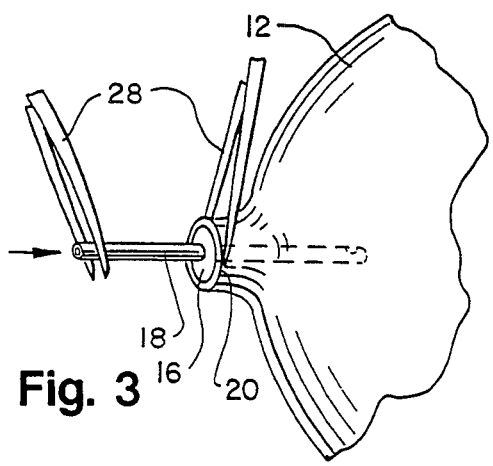
Fig. 3
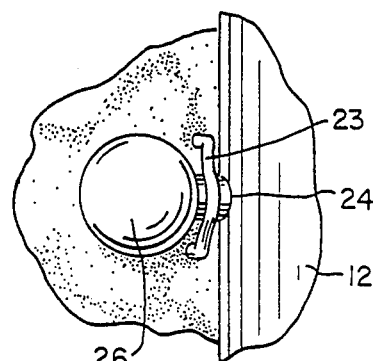
Fig. 4
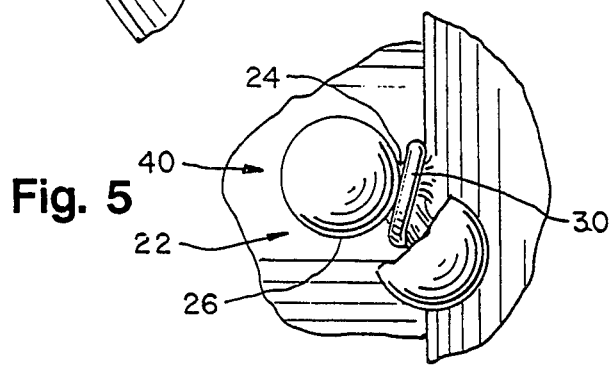
Fig. 5
Fig. 6
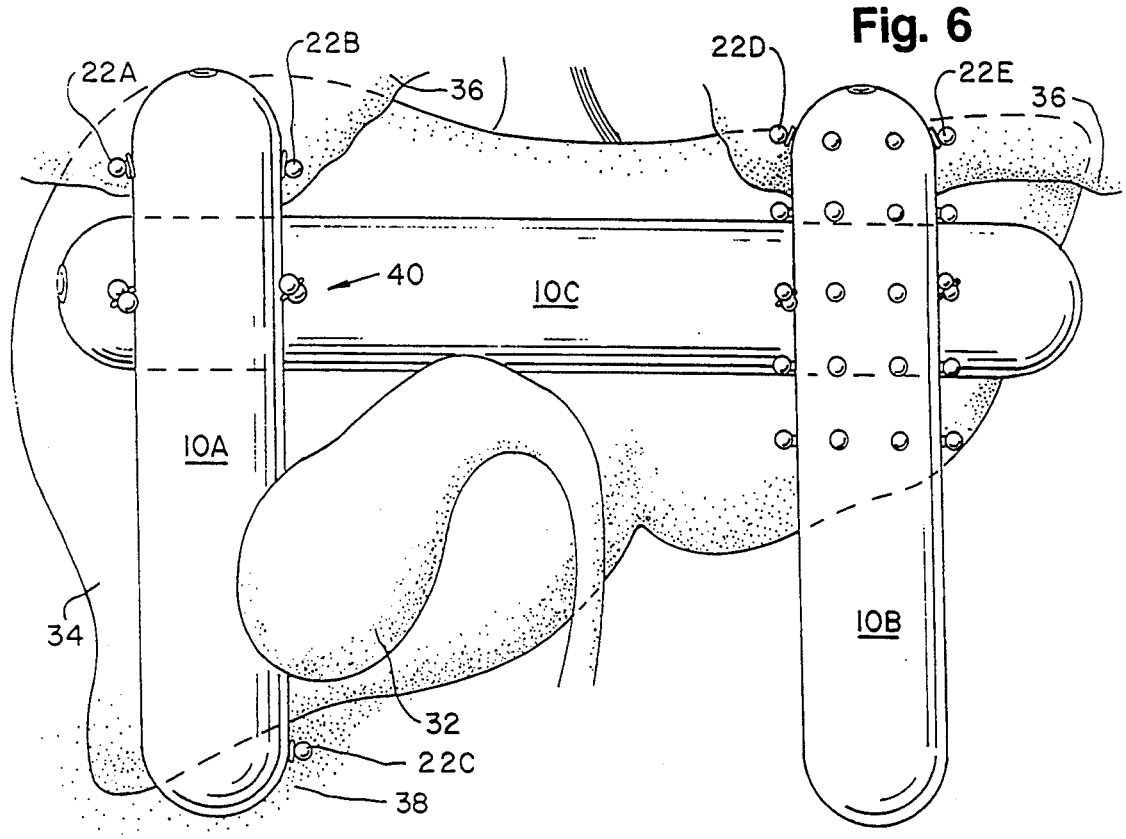

RETRACTOR FOR ENDOSCOPIC SURGERY

This is a continuation of U.S. patent application Ser. No. 997,655, filed Dec. 28, 1992, now abandoned, which is a continuation of U.S. patent application Ser. No. 650,049, filed Feb. 4, 1991, now abandoned.

BACKGROUND OF THE INVENTION

This invention relates to a retractor for endoscopic surgery.

During internal surgery it is often necessary to alter the position of various organs or tissues to provide access to the tissues which are the subject of the surgery. It is also necessary to hold the organs or tissues which have been so moved in a stable position during the surgery so that movement thereof will not interfere with the work of the surgeon or surgical assistants.

Devices which move and hold viscera for this purpose are referred to as surgical retractors because of their function of retracting the interfering tissues from the operating field. A number of such devices exist for use where a relatively large incision has been made in the subject's body. Often these devices have broad surfaces to distribute the forces they exert on the viscera over larger areas and thus minimize trauma. One such retractor is shown in U.S. Pat. No. 4,889,107.

In endoscopic surgery only small incisions are made, thereby minimizing trauma and post-operative pain. An endoscope is used to illuminate the internal organs and tissues and provide the surgeon with visual feedback which may be magnified and displayed optically and electronically. Surgical instruments are introduced through flexible tubes or trocars or the operating channel of an endoscope, which may be only 1 cm. in diameter, and are remotely manipulated by the surgeon.

Conventional retractors are too large to enter the body through the small incisions made in endoscopic surgery and in some cases may be disproportionate in size to the tissues to be retracted. Accordingly it is common to reposition tissues using very small forceps to push or pull the tissues which, however, increases the risk of injury or trauma.

Inflatable or collapsible devices or balloon have been used in surgery or body treatment for various purposes. A surgical retractor for conventional surgery which collapses for ease of removal just before final closure is shown in U.S. Pat. No. 3,863,639. Balloons have also been inserted in the body for a variety of large scale applications such as opening passageways, as seen in U.S. Pat. Nos. 4,312,353; 4,714,074; 4,800,901 and 4,899,747. One inflatable device for use in propelling an endoscope through a body passage is shown in U.S. Pat. No. 4,207,872.

BRIEF DESCRIPTION OF THE DRAWINGS

FIG. 1 is a perspective view of a surgical retractor according to the present invention in its deflated state with the central portion omitted.

FIG. 2 is a perspective view of the surgical retractor of FIG. 1 in its inflated state with the central portion omitted for clarity.

FIG. 3 is a detailed perspective view showing the inflation process for the surgical retractor shown in FIGS. 1 and 2.

FIG. 4 is a detailed perspective view of a protrusion on the surgical retractor of FIGS. 1 and 2 fastened to tissue.

FIG. 5 is a detailed fragmentary perspective view of the fastening of two surgical retractors as shown in FIGS. 1 and 2 to one another.

FIG. 6 is a stylized perspective view of a surgical retractor system according to the present invention in position during surgery, with some of the protrusions omitted for clarity.

SUMMARY OF THE INVENTION

The present invention provides a surgical retractor which is particularly useful in endoscopic surgery and provides, as required, both the functions of moving tissues and retaining them outside of the surgical field. The invention also provides a system for and a method of surgical retraction utilizing such surgical retractors.

DETAILED DESCRIPTION

Referring in more particularity to the drawings, a surgical retractor 10 according to the invention comprises an elastic skin 12, desirably formed of an inert material such as medical grade synthetic rubber which will not react with or injure body tissues or fluids. The skin should be substantially impervious to fluids so that it will contain a gas such as carbon dioxide or a liquid such as water which is injected into it to inflate it as described below. The skin should be soft and smooth to minimize damage to the tissues it contacts, physically stable on its exterior so as to minimize particles being rubbed off or flaking into the patient's body and strong enough to withstand the expansive forces exerted by the fluid. The skin should be as thin as practicable in consideration of these requirements so as to facilitate its compression when it is deflated into a narrow package for insertion into the subject's body through a narrow tube such as a trocar.

The skin 12 encloses a variable volume cavity 14 which may approach zero in volume when the skin is flattened and compressed. In FIG. 2 the cavity 14 is shown as being substantially larger as a result of introduction of a liquid or gas, which has inflated the skin as described below. When the skin 12 is flattened and compressed, it is rolled or otherwise packed into a package having a diameter small enough that it can be pushed through a narrow tube such as a trocar into the patient's body. There, using forceps or other grasping inplements it is unrolled to the flat configuration and placed adjacent the tissues to be retracted.

As illustrated, the skin 12 may be inflated by a needle on a polyethelene tube to provide a narrow substantially cylindrical shape. Other predetermined shapes could be utilized such as spheres, discs, or cylindrical or bulbous portions connected by narrower necks. Although such shapes could be useful in particular operating situations, it is believed that the narrow cylindrical shape illustrated is useful in the greatest variety of operating conditions and is usually the most useful for construction of retractor systems using more than one retractor as described below.

The skin includes a plug portion 16 formed of a self sealing material to facilitate, first, a puncture by a needle 18 or other injection device (FIG. 3) by means of which gas or fluid is introduced into the cavity 14 to inflate the skin 12 and, second, an inherent sealing action upon withdrawal of the needle 18 so that the gas or fluid is retained within the skin 12. It is desirable that the plug be easily and securely grasped during the fluid injection process. This quality may be provided by selection of a substantially rigid material for the plug.

However, if there is a conflict between the needs for rigidity and self sealing qualities, the plug 16 may be surrounded by a more rigid ring 20 for secure grasping. Such material characteristics desirable for the skin such as inertness, non-reactivity in the body, imperviousness and exterior physical stability are also desirable for the plug and ring.

The plug, ring and skin are desirably formed of a single piece of material to minimize the possibility of leakage of the fluid at joints between such members. To the extent that this may be impracticable or uneconomical in manufacture there should be secure sealing at the points of joinder of the three pieces.

An important feature of the present invention is the provision of at least one protrusion and preferably a plurality of protrusions 22 extending outwardly from the skin. As illustrated, each protrusion comprises a shaft 24 extending outwardly from the outer surface of the skin terminating in a bulb or bulbous portion 26 having larger dimensions parallel to the surface of the skin 12 than those of the shaft. FIG. 4 illustrates the utility of this construction in fastening the skin to body tissue. A surgical staple 23 is fitted on the shaft 24, penetrates the underlying tissue and is closed. The greater dimensions of the bulb 26 and the skin 12 relative to the diameter of the shaft 24 anchor the assembly to the body tissue, even if there is not a completely rigid engagement of the tissue, staple and shaft. Surgical clips, sutures or other fastening means could also be used instead of staples. One embodiment of a clip or staple could have a ring on the staple, so that multiple staples could be positioned on a hook and introduced to the surgical site. The staples could be removed from the hook as needed, which would eliminate the need to introduce staples to the surgical site through the trocar one at a time.

The protrusions 22 may be hollow and elastic and define volumes connected with and inflatable along with the variable volume cavity 14. Alternatively, the protrusions may be solid pieces with the bulbs being either three dimensional or flat pieces. In either case, it is desirable that they be integral with and of the same material as the skin 12 to avoid a multiplicity of seals. There are advantages and disadvantages with both designs which will influence the selections made by manufacturers and surgeons. Solid protrusions are believed to be simpler and less expensive to manufacture, using such processes as coating a mandrel with latex prior to curing, than are hollow protrusions. However solid protrusions provide less secure attachment to tissues if the bulbs 26 are flat or merely two dimensional. If the bulbs are three dimensional the increased bulk may present difficulties in compressing the retractor sufficiently for passage through the access tube. In addition, solid protrusions can cause undesirable pressure concentrations on delicate tissues. On the other hand, if the shafts 24 are inflatable there may be an increased risk of puncture by the fastening means.

In a preferred embodiment of the invention, as shown in FIG. 1 and FIG. 2, a skin 12 is substantially cylindrical in shape when inflated and is approximately 15 cm. long with a diameter of about 5 cm. There are eight rows of protrusions spaced circumferentially around the cylinder with angular spacing of about 45 degrees between each row. Each row has 15 protrusions spaced longitudinally about 1 cm. from one another. Thus, 90 protrusions are provided for attachment. If the retractor is placed in intimate contact over its entire length with an organ with two rows of protrusions, one on each side, adjacent the organ, 30 protrusions in two rows of 15 spaced about 1cm. apart, are available for fastening to the organ or other tissues at appropriate points based on medical considerations. Protrusions on the two intermediate rows are available for fastening to other tissues. The plug and ring are preferably about 0.5 cm. in diameter, sufficiently small to be moved through a tube used for endoscopic surgery.

In operation the retractor is flattened as shown in FIG. 1 and is rolled or compressed into a configuration narrow enough to be pushed through a narrow tube or trocar extending through an incision into the patient's body. The retractor may be pre-packaged in this configuration by the manufacturer. After being pushed out of the tube, the retractor is unrolled and placed in a preliminary position adjacent the organ or tissues to be retracted. As shown in FIG. 3 a pair of laparoscopic forceps 28 are used to grasp the plug 16 and ring 20 and the injection device or needle 18. The needle 18 is inserted through the plug 16 into the variable volume cavity 14. Through controls (not shown) an injection of gas such a carbon dioxide or a fluid through the needle begins which starts to inflate the skin 12. As the skin inflates it will exert pressure against the adjacent organ and move it. The exact details of the process are a product of the surgeon's exercise of professional skills and judgment and the size and placement of the organs to be retracted. In most cases there will be an iterative process of partial inflation, repositioning of the retractor, fastening by staples or other means and further inflation etc. until the organs are in their desired relative positions and stably held by the retractor. After the desired inflation is achieved the needle is withdrawn and the puncture sealed by the self sealing action of the plug.

Another important feature and advantage of the invention resides in the attribute that the protrusions of two or more retractors may be utilized to fasten two retractors together as shown in FIG. 5. This enables the surgeon to actually construct a customized structure of retractors for each patient considering his unique body structure and surgical needs. Thus the invention provides a system and method of surgical retraction usable in a variety of situations and patients. One such method and system is shown in FIG. 6. However this is only exemplary of an infinite number of uses of the method and system. The system of the present invention is ideally suited for perfoming pelvic surgery, and in particular, endoscopic pelvic surgery. For example, the small bowel and cecum may first be pushed out of the pelvis as the operating table is tilted head down. The inflatable retractors are then partially inflated and stapled to the anterior abdominal wall and side abdominal walls. Posteriorly, the peritoneum is picked up, and a staple is applied so that only the peritoneum is stapled to the protrusionss of the retractor, and special care is taken over the ureters and inferior vena cava. As the the retractor is inflated, the surgeon watches to see that the vena cava is not occluded or compressed. No staples are placed over the vena cava or rectum, of course. Clips are placed where the protrusions of one retractor overlap the protrusions of an adjacent retractor. When inflated, a solid wall of retractors keep the vicera out of the pelvis.

FIG. 5 is a fragmentary perspective view of two of the surgical retractors 10 shown in FIGS. 1 and 2 located at a substantially right angle to one another. As shown, the shafts 24 of two protrusions 22 also cross one another and are fastened to one another by a surgical clip 30.

FIG. 6 illustrates the use of multiple retractors according to the invention in a laparoscopic cholecystectomy, that is, surgery to remove the gall bladder. Typically, access to the gall bladder 32 requires retraction of the liver 34 which overlies the gall bladder viewed from the patient's front. A first retractor 10A is inserted and placed overlying the large right lobe of the liver. After partial inflation and positional adjustment relative to the liver, protrusions 22A and 22B are fastened to the patient's anterior abdominal wall 36 and protrusion 22C is fastened to the patient's posterior peritoneum and the underlying fascia, under the right lobe of the liver. Retractor 10A is further inflated, thus pushing the lower right lobe of the liver anteriorly. This movement may suffice of itself to expose the gall bladder for surgery. If not, a second retractor 10B is inserted, partially inflated, placed anteriorly to the smaller left liver lobe and fastened using protrusions 22D and 22E to the anterior abdominal wall 36 over the medial portion of the liver. Full inflation of retractor 10B provides additional forcing of the liver to the posterior to expose the gall bladder. In some cases it may be necessary to retract the liver toward the patient's head. In such a case, as illustrated, a third retractor 10C is placed posteriorly of the two retractors 10A and 10B and anteriorly of the liver 34. Retractor 10C is fastened to the other retractors as indicated at 40 and shown in detail in FIG. 5. Thereupon inflation of retractor 10C forces the liver in the cephalid direction.

As may be seen from the foregoing example, surgical retractors according to the invention may be arranged in numerous combinations to exert forces on, move and hold various organs or parts of organs for surgery. The retractors may be arranged to exert parallel, opposing or complementary forces and some retractors may serve as load bearing bases supporting the actions of other retractors.

In all applications, upon completion of the surgery the retraction is reversed by deflating the retractors by puncturing them using a needle or laser. Upon deflation they may be grasped and removed through the trocar or incision.

Although the foregoing has described various embodiments of the invention in detail, those skilled in the art will understand that many of these details may be varied without departing from the scope of the invention.

I claim:

1. A surgical retractor comprising an elastic skin enclosing a variable volume cavity, said skin being movable through a narrow passageway when said enclosed volume is low, said skin including a plurality of outward projections for cooperation with a mechanical fastening means, and said projection comprising the same material from which the elastic skin is formed.

2. A surgical retractor according to claim 1 wherein each projection comprises a shaft adjacent said enclosed volume and a bulbous head at the outward end of said shaft.

3. A surgical retractor according to claim 2 wherein said shaft is engageable by a fastening means whereby said retractor is fasteneable to tissues or other surgical retractors.

4. A surgical retractor according to claim 1 wherein said skin is elongated in one dimension relative to its other two dimensions to form a substantially cylindrical shape when the skin is inflated.

5. A surgical retractor according to claim 4 wherein said projections are disposed in substantially longitudinal rows along the elongated dimension of said skin and in substantially circumferential rows around said cylindrical shape.

6. A surgical retractor according to claim 1 wherein said projections are non-inflatable flaps.

7. A surgical retractor according to claim 1 wherein said projections define portions of the variable volume cavity enclosed by said skin.

8. A surgical retractor system comprising at least two surgical retractors, each of said surgical retractors comprising a collapsible and inflatable balloon, means for permitting introduction of a gas of fluid into said balloon whereby said balloon may be inflated and for sealing said balloon after said introduction of fluid to prevent deflation thereof, wherein each of said balloons has a substantially cylindrical shape and a plurality of outward projections whereby each of said balloons may be mechanically attached to one another or to body tissues, each projection comprising the same material from which the balloon is formed, said outward projections to facilitate attachment of said balloons to tissues and to one another to form a retaining structure.

9. A method of retraction for endoscopic surgery comprising introducing a deflated balloon having outward projections thereon into a cavity of a body adjacent to tissues to be retracted from a surgical field, wherein the projections comprise the same material from which the balloon is formed, inflating said balloon to alter the position of said tissues, and mechanically fastening at least one of said projections to said body to retain said tissues in the altered positions.

10. The method of retraction for endoscopic surgery according to claim 9 further comprising, introducing at least an additional deflated balloon having outward projections thereon into a cavity of a body adjacent to tissues to be retracted from a surgical field, fastening at least one projection of said additional balloon to a projection of the first balloon, and inflating said additional balloon to alter the position of said tissue.

11. A method of retraction for endoscopic surgery comprising the steps of:

providing a trocar inserted into an incision into a patient's body;

providing an elastic skin enclosing a variable volume cavity, wherein the elastic skin further comprises at least one outward projection for cooperation with a fastening means, and each projection comprises the same material from which the elastic skin is formed;

inserting the deflated elastic skin through the trocar into a patient's body;

positioning the elastic skin near tissue to be retracted;

inflating the elastic skin to alter the position of the tissue;

deflating the elastic skin; and removing the elastic skin from a patient's body through the trocar.

12. A method of retracting tissue during endoscopic surgery comprising the steps of:

making an incision into a patient's body, placing a trocar into the incision, inserting into the patient's body through the trocar an elastic skin enclosing a variable volume cavity, the elastic skin having connected thereto inflation means, positioning the elastic skin against tissue to be retracted, inflating the elastic skin such that the tissue is thereby retracted from a surgical field.

* * * * *